United States Patent
Tanenbaum et al.

(10) Patent No.: US 10,441,696 B2
(45) Date of Patent: Oct. 15, 2019

(54) VOICE INTERFACE FOR A DIALYSIS MACHINE

(71) Applicant: Fresenius Medical Care Holdings, Inc., Waltham, MA (US)

(72) Inventors: Lee Daniel Tanenbaum, Walnut Creek, CA (US); Fei Wang, Concord, CA (US); Mario Gumina, Danville, CA (US); Thomas Merics, Antioch, CA (US); Eric Hoffstetter, Pleasanton, CA (US); Matthew Doyle, Concord, CA (US); Aleo Nobel Mok, Orinda, CA (US); Wayne Raiford, Vallejo, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 58 days.

(21) Appl. No.: 15/806,994

(22) Filed: Nov. 8, 2017

(65) Prior Publication Data
US 2018/0064865 A1      Mar. 8, 2018

Related U.S. Application Data

(63) Continuation of application No. 14/847,210, filed on Sep. 8, 2015, now Pat. No. 9,839,735.

(51) Int. Cl.
| | | |
|---|---|---|
| G10L 17/00 | (2013.01) | |
| A61M 1/14 | (2006.01) | |
| G10L 17/22 | (2013.01) | |
| G06F 3/16 | (2006.01) | |
| G10L 15/22 | (2006.01) | |
| A61M 1/16 | (2006.01) | |
| G16H 40/63 | (2018.01) | |
| G06F 19/00 | (2018.01) | |
| A61M 1/28 | (2006.01) | |

(52) U.S. Cl.
CPC ............ *A61M 1/14* (2013.01); *A61M 1/1601* (2014.02); *A61M 1/28* (2013.01); *G06F 3/167* (2013.01); *G06F 19/3481* (2013.01); *G10L 15/22* (2013.01); *G10L 17/22* (2013.01); *G16H 40/63* (2018.01); *A61M 2205/3569* (2013.01); *A61M 2205/3592* (2013.01); *A61M 2205/50* (2013.01); *A61M 2205/502* (2013.01); *A61M 2205/80* (2013.01); *G10L 2015/223* (2013.01)

(58) Field of Classification Search
None
See application file for complete search history.

(56) References Cited

U.S. PATENT DOCUMENTS

| | | |
|---|---|---|
| 5,970,457 A | 10/1999 | Brant et al. |
| 6,173,259 B1 | 1/2001 | Bijl et al. |
| (Continued) | | |

FOREIGN PATENT DOCUMENTS

| | | |
|---|---|---|
| DE | 196 24 988 | 1/1998 |
| EP | 2189977 | 5/2010 |
| WO | WO 2008/042118 | 4/2008 |

*Primary Examiner* — Satwant K Singh
(74) *Attorney, Agent, or Firm* — Fish & Richardson P.C.

(57) ABSTRACT

A dialysis system, comprising: a dialysis machine; an authentication component configured to determine that a source of a voice command received by the dialysis system is an authorized user of the dialysis system; and a processor configured to carry out a function determined based on the voice command.

16 Claims, 12 Drawing Sheets

(56) References Cited

U.S. PATENT DOCUMENTS

| | | | |
|---|---|---|---|
| 6,811,707 B2* | 11/2004 | Rovatti | A61M 1/16 210/739 |
| 7,088,233 B2 | 8/2006 | Menard | |
| 7,138,902 B2 | 11/2006 | Menard | |
| 7,286,992 B2 | 10/2007 | Sander et al. | |
| 7,540,851 B2 | 6/2009 | O'Mahony et al. | |
| 7,918,993 B2 | 4/2011 | Harraway | |
| 8,287,724 B2 | 10/2012 | Slepicka et al. | |
| 8,330,579 B2 | 12/2012 | Kneip | |
| 8,769,625 B2* | 7/2014 | Wang | G06F 19/3418 726/4 |
| 9,165,112 B2 | 10/2015 | Doyle | |
| 9,178,891 B2 | 11/2015 | Wang | |
| 9,635,111 B2 | 4/2017 | Wang | |
| 9,839,735 B2* | 12/2017 | Tanenbaum | A61M 1/14 |
| 2007/0080801 A1 | 4/2007 | Weismiller | |
| 2008/0209357 A1* | 8/2008 | Vasta | A61M 1/16 715/771 |
| 2009/0275883 A1* | 11/2009 | Chapman | A61M 1/28 604/29 |
| 2010/0312174 A1 | 12/2010 | Hoffman | |
| 2012/0138533 A1 | 6/2012 | Curtis | |
| 2012/0154264 A1* | 6/2012 | Wang | A61M 1/16 345/156 |
| 2013/0037461 A1 | 2/2013 | Biewer et al. | |
| 2013/0201222 A1 | 8/2013 | Doyle et al. | |
| 2013/0317420 A1 | 11/2013 | Wehmeyer | |
| 2014/0148104 A1 | 5/2014 | Marterstock | |
| 2014/0205981 A1* | 7/2014 | Ryder | G09B 19/00 434/262 |
| 2014/0266983 A1 | 9/2014 | Christensen | |
| 2014/0267003 A1 | 9/2014 | Wang et al. | |
| 2014/0309612 A1 | 10/2014 | Smisson et al. | |
| 2015/0253860 A1 | 9/2015 | Merics et al. | |
| 2017/0039423 A1 | 2/2017 | Cork | |

* cited by examiner

VOICE INTERFACE FOR A DIALYSIS MACHINE

CROSS-REFERENCE TO RELATED APPLICATION

This application is a continuation and claims the priority of U.S. Ser. No. 14/847,210, filed Sep. 8, 2015, the entire contents of which are incorporated by reference herein.

TECHNICAL FIELD

This disclosure relates to a voice interface for a dialysis machine.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

Dialysis machines are typically equipped with interfaces for receiving inputs and providing information to users.

SUMMARY

In one aspect, a dialysis system includes a dialysis machine. The dialysis system also includes an authentication component configured to determine that a source of a voice command received by the dialysis system is an authorized user of the dialysis system. The dialysis system also includes a processor configured to carry out a function determined based on the voice command.

Implementations can include one or more of the following features.

In some implementations, the dialysis system also includes a voice recognition component configured to identify the voice command in audio information received by a microphone.

In some implementations, the voice command includes a command for the dialysis machine to perform a dialysis function.

In some implementations, audio information from which the voice command is identified is received by the dialysis system from an external device.

In some implementations, the external device includes a microphone.

In some implementations, the dialysis system includes the microphone.

In some implementations, the authentication component is configured to receive input from a non-voice interface of the dialysis system and determine that the input is received from an authorized user.

In some implementations, the authentication component is configured to receive an indication that an authorized user is in proximity to the dialysis system.

In some implementations, the voice recognition component has one of two states: i) an enabled state in which the voice recognition component is configured to identify the voice command in the audio information, and ii) a standby state in which the voice recognition component is configured to not identify the voice command in the audio information.

In some implementations, the voice recognition component is configured to identify a wakeup command in the audio information received by the microphone when the voice recognition component is in the standby state.

In some implementations, the voice recognition component enters the enabled state when the voice recognition component identifies the wakeup command.

In some implementations, the voice recognition component is in the sleep state when an authorized user is not in proximity to the dialysis system.

In some implementations, the indication that an authorized user is in proximity to the dialysis system is based on the receiving of data associated with an external tag.

In some implementations, the external tag includes an RFID tag.

In some implementations, the authentication component is configured to determine that the source of the voice command is an authorized user of the dialysis system based on data identifying the source of the voice command.

In some implementations, the data identifying the source of the voice command is based on a voice code in audio information received by a microphone.

In some implementations, the data identifying the source of the voice command is based on an identification card containing a data storage medium that can be accessed by the dialysis system.

In some implementations, the processor is configured to determine whether the dialysis function is authorized to be carried out in response to the voice command being identified.

In some implementations, the dialysis system also includes a user interface component configured to cause a user interface to display an arrangement of user interface elements.

In some implementations, the user interface elements are buttons displayed by the user interface, and the voice command includes a command to rearrange the buttons.

In some implementations, the command to rearrange buttons causes a button of the dialysis machine to be replaced with a different button.

In some implementations, the command to rearrange buttons causes a first button of the dialysis machine and a second button of the dialysis machine to be combined into a single button that, when interacted with, causes the dialysis system to perform at least one action associated with the first button and at least one action associated with the second button.

In some implementations, the command to rearrange buttons includes a reference to a stored profile that defines an arrangement of buttons to be displayed.

In some implementations, the command to rearrange buttons includes a reference to a stored profile that defines a particular button to be displayed.

In some implementations, the command to rearrange buttons is carried out based at least in part on an identity of the source of the voice command.

In some implementations, the command to rearrange buttons is associated with a stored profile associated with the source of the voice command.

In some implementations, the user interface component is configured to cause the user interface to display an arrangement of user interface elements that is based on an identity of the source of the voice command.

In another aspect, a dialysis system includes a dialysis machine. The dialysis system also includes a speaker. The dialysis system also includes an alarm component configured to determine that an alarm condition related to the dialysis machine exists, and cause the speaker to provide spoken information related to the alarm condition.

Implementations can include one or more of the following features.

In some implementations, the spoken information includes an identification of the dialysis machine.

In some implementations, the spoken information includes an identification of a location of the dialysis machine.

In some implementations, the alarm component is configured to determine the spoken information based on a verbosity setting of the dialysis system.

In some implementations, the verbosity setting is determined based on an identity of a user of the dialysis system.

In some implementations, the verbosity setting is determined based on a medical qualification of a user of the dialysis system.

In another aspect, a dialysis system includes a dialysis machine. The dialysis system also includes a speaker. The dialysis system also includes an instruction component configured to determine that an action has not yet been completed, and cause the speaker to provide spoken instructions that assist a user of the dialysis system in completing the action.

Implementations can include one or more of the following features.

In some implementations, the instruction component is configured to determine the spoken instructions based on a verbosity setting of the dialysis system.

In some implementations, the verbosity setting is determined based on an identity of the user.

In some implementations, the verbosity setting is determined based on a medical qualification of the user.

In some implementations, the instruction component is configured to cause the speaker to provide subsequent spoken instructions that assist the user of the dialysis system in completing a second action.

In some implementations, the subsequent spoken instructions are provided a predetermined amount of time after the spoken instructions are provided.

In some implementations, the dialysis system also includes a display that is configured to provide visual information related to the action.

In some implementations, the visual information is one or both of an image and a video that show the action being at least partially completed.

Implementations can include one or more of the following advantages.

In some implementations, the systems and techniques described herein can promote cleanliness and sterilization in a dialysis environment. For example, a user who issues a voice command to the dialysis system does not need to make physical contact with the dialysis system to control it, thereby reducing the risk of spreading germs and eliminating the need for the user to wear gloves.

In some implementations, dialysis systems with voice command capability allow a user to quickly provide instructions to multiple different dialysis systems that are spatially separated rather than, for example, approach a physical user interface of each dialysis system.

In some implementations, dialysis system with voice alarm capability allow a user (e.g., a caregiver or a guardian) to learn detailed information related to alarm conditions when the user is not in immediate proximity to the dialysis system. For example, such as in a home dialysis context, a guardian can temporarily leave a patient alone and still receive detailed alarm information that indicates the critical nature of the particular alarm condition.

In some implementations, dialysis systems with voice alarm capability can assist a caregiver in differentiating various alarm that may be occurring concurrently on multiple machines. For example, the caregiver can quickly identify the nature of each alarm condition, determine which alarm condition is most critical, and provide assistance according to need.

In some implementations, dialysis systems with voice instruction capability can assist a user in performing dialysis set up actions, treatment actions, and calibration actions. For example, the user can perform a particular action at the direction of the voice instruction without having his or her attention diverted by the need to read written instructions. The adjustable nature of the verbosity of the voice instructions allows the dialysis system to provide instructions that are tailored to a particular user or a particular type of user (e.g., a caregiver, a patient, a technician, etc.), thereby increasing the efficiency of performing the action.

Other aspects, features, and advantages of the invention will be apparent from the description and drawings, and from the claims.

DESCRIPTION OF DRAWINGS

Like reference symbols in the various drawings indicate like elements.

DETAILED DESCRIPTION

A dialysis machine can include a microphone and a component that provide voice recognition capabilities to the machine. For example, in some implementations, the component is configured to identify voice commands that are issued by a user. The voice command may cause the dialysis machine to carry out a dialysis function. Alternatively, the voice command may cause a user interface of the dialysis machine (e.g., a display, such as a touchscreen display) to be adjusted. The dialysis machine may have its voice recognition capabilities active only when the user is within proximity of the machine. The voice recognition capabilities allow the user to control the machine without touching the machine, thereby eliminating the need for the user to wear gloves and/or reducing the risk of facilitating the spread of infection that is more likely to occur when using a touch-based input device.

A dialysis machine can also include a speaker for providing spoken information to a user. For example, in some implementations, the speaker can provide spoken instructions to assist the user in machine set-up, calibration, and/or operation. Such spoken instructions can be particularly useful in a home dialysis setting. In some implementations, the speaker can provide spoken alarms that are related to alarm conditions. The spoken alarms may include patient and/or dialysis machine identifying information. The verbosity of the spoken instructions and/or the spoken alarms may be adjustable, and both may be accompanied by visual information displayed by the dialysis machine (e.g., visual alarms, images, and/or videos). In some implementations, the speaker may include a unit with one or more processors to process received input that is used in connection with providing the spoken information.

Figure 1:
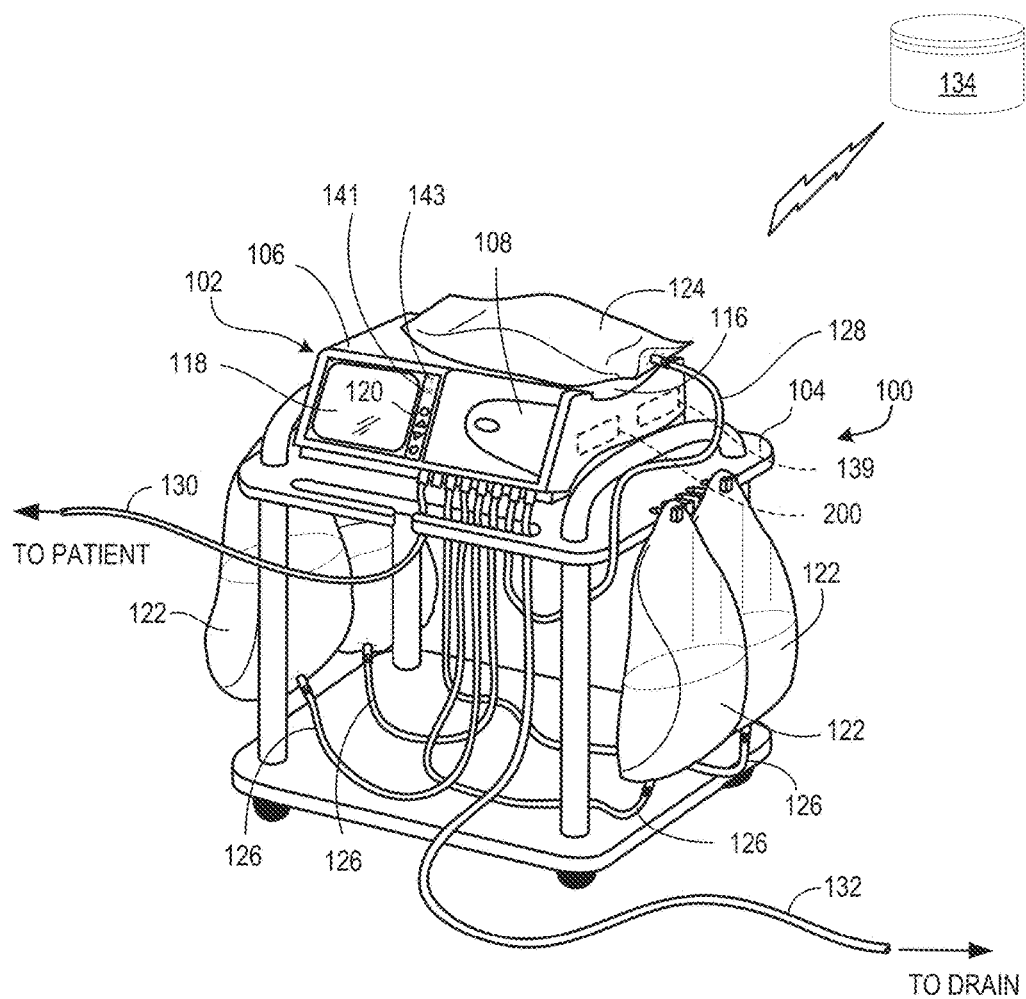
FIG. 1 shows an example of a peritoneal dialysis system.

FIG. 1 shows a peritoneal dialysis ("PD") system 100 that includes a PD machine (also referred to as a PD cycler) 102 seated on a cart 104. The PD machine 102 includes a housing 106, a door 108, and a cassette interface that contacts a disposable PD cassette when the cassette is disposed within a cassette compartment formed between the cassette interface and the closed door 108. A heater tray 116 is positioned on top of the housing 106. The heater tray 116 is sized and shaped to accommodate a bag of dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette via dialysate bag lines 126 and a heater bag line 128, respectively. The dialysate bag lines 126 can be used to pass dialysate from dialysate bags 122 to the cassette during use, and the heater bag line 128 can be used to pass dialysate back and forth between the cassette and the heater bag 124 during use. In addition, a patient line 130 and a drain line 132 are connected to the cassette. The patient line 130 can be connected to a patient's abdomen via a catheter and can be used to pass dialysate back and forth between the cassette and the patient's peritoneal cavity during use. The drain line 132 can be connected to a drain or drain receptacle and can be used to pass dialysate from the cassette to the drain or drain receptacle during use.

The PD machine 102 also includes a control unit 139 (e.g., a processor), a speaker 141, and a microphone 143. The control unit 139 can receive signals from and transmit signals to the touch screen display 118, the control panel 120, the speaker 141, the microphone 143, and the various other components of the PD system 100. The PD machine 102 can receive audio input (e.g., spoken commands) through the microphone 143 and provide audio output (e.g., spoken alarms, alerts, and instructions) through the speaker 141. The control unit 139 can control the operating parameters of the PD machine 102, for example, based in part on the audio input and output. In some implementations, the control unit 139 is an MPC823 PowerPC device manufactured by Motorola, Inc.

Voice Commands

Figure 2:
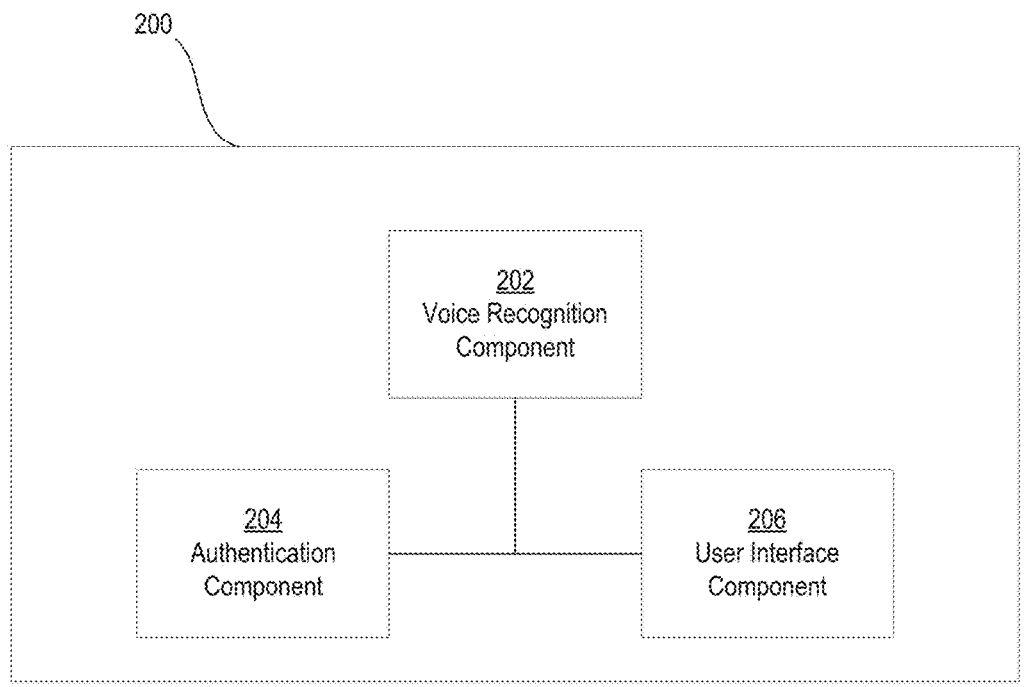
FIG. 2 shows an example of a processing component of the dialysis system of FIG. 1 that includes a voice recognition component, an authentication component, and a user interface component.

The PD system 100 also includes a processing component. An example of a processing component 200 is shown in FIG. 2. The processing component 200 is configured to recognize and process voice commands. In this example, the processing component 200 includes a voice recognition component 202, an authentication component 204, and a user interface component 206. The processing component 200 is configured to communicate with the control unit 139, the microphone 143, and the touch screen display 118 of FIG. 1.

The microphone 143 is configured to receive audio information (e.g., spoken information) from a user, such as a patient or a caregiver. The voice recognition component 202 can receive the audio information from the microphone 143 and identify one or more voice commands in the audio information. In some implementations, a message (e.g., an audio message or a visual message) is presented if the voice command is not understood or not permitted. The voice recognition component 202 is configured to translate the audio information into text. The translated text is compared to stored information (e.g., stored text) that corresponds to one or more voice commands. The stored information may include verbal sound patterns expected/associated with various voice commands. For example, the voice recognition component 202 may translate audio information into a text string "set dialysate flow rate to 500 milliliters per minute." The stored text may include the text string "set dialysate flow rate" and information linking the text string to a "set dialysate flow rate" voice command. The spoken text string is compared to the stored text string, and based on the comparison, invocation of the "set dialysate flow rate" voice command is identified. The control unit 139 can then provide instructions for causing the dialysis system 100 to carry out a function related to the voice command. The text to which the translated text is compared may be stored on the dialysis machine 102 and/or stored in a location accessible by the dialysis system 100 (e.g., on a server, in a database, etc.). For example, a command storage 134 can store data referencing commands that are associated with particular text strings. The command storage 134 can be external to the dialysis machine 102 (e.g., as shown in FIG. 1) or may be included as part of the dialysis machine 102.

One or more of the voice commands that correspond to the stored information may be commands for the dialysis machine 102 to perform a dialysis function. For example, the voice commands may include a command for setting the dialysate flow rate (e.g., "set dialysate flow rate to 500 milliliters per minute"), a command for setting the heparin infusion rate (e.g., "set heparin infusion rate to 21 milliliters per hour"), a command for running a heat disinfection procedure (e.g., "run heat disinfect"), a command for raising dialysate conductivity limits (e.g., "set upper conductivity limit to 14.5 mS/cm"), and a command for initiating a sustained low-efficiency dialysis ("SLED") treatment program (e.g., "run SLED"), among others. In some implementations, one or more of the voice commands are related to other (e.g., non-dialysis) functions such as maintenance functions and/or cleaning functions, among others, as described in more detail below. In some implementations, the source of the voice command (e.g., a person who issues the voice command) provides a confirmation (e.g., by saying "confirm") before the control unit 139 carries out the function related to the voice command.

One or more of the voice commands may be associated with a parameter or multiple parameters. For example, the "set dialysate flow rate" is associated with a dialysate flow rate parameter. Thus, part of identifying the "set dialysate flow rate" voice command includes identifying the provided value for the dialysate flow rate parameter, which is "500 milliliters per minute" in this example. The control unit 139 can then provide instructions to the dialysis system 100 to cause the dialysis system 100 to carry out a function related to the voice command (e.g., set the dialysate flow rate to 500 milliliters per minute).

In some implementations, one or more of the voice commands may be for configuring a user interface of the dialysis system 100 (e.g., the touch screen display 118 of FIG. 1). The user interface component 206 may be configured to cause the user interface to display an arrangement of user interface elements (e.g., buttons) in response to a voice command. For example, the user interface component 206 may cause a display to present an arrangement of buttons that a user can interact with to control the dialysis system 100. In some implementations, the voice command may cause the buttons to be rearranged. For example, the voice command may cause one button to be replaced with a different button (e.g., "replace the 'dialysate flow' button with the 'ultrafiltration removed' button"). The voice command may cause a first button and a second button to be combined into a single button (e.g., "combine the 'ultrafiltration rate' button and the 'ultrafiltration time' button"). A combined button may represent multiple actions that are typically performed together. The dialysis system 100 may perform at least one action associated with the first button and at least one action associated with the second button when the user interacts with the single combined button.

Figure 3A:
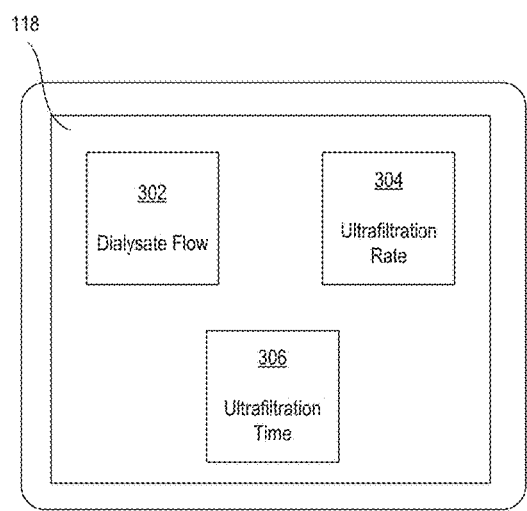
FIGS. 3A-3B show examples of a user interface of the dialysis system of FIG. 1.
Figure 3B:
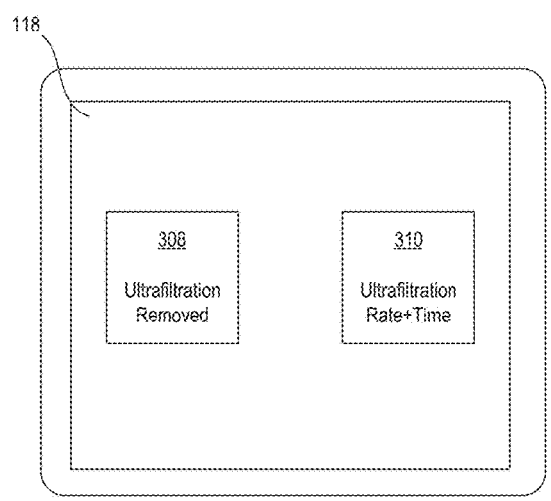

FIGS. 3A and 3B show examples of the touch screen display 118 according to configurations consistent with the example provided above. In FIG. 3A, the touch screen display 118 presents a 'dialysate flow' button 302, an 'ultrafiltration rate' button 304, and an 'ultrafiltration time' button 306. A user who wishes to alter the configuration of the touch screen display 118 may issue the following commands: i) "replace the 'dialysate flow' button with the 'ultrafiltration removed' button" and ii) "combine the 'ultrafiltration rate' button and the 'ultrafiltration time' button."

The user interface component 206 causes the touch screen display 118 to adjust the arrangement of buttons according to the presentation shown in FIG. 3B. Specifically, the 'dialysate flow' button 302 is replaced with an 'ultrafiltration removed' button 308, and the 'ultrafiltration rate' button 304 and the 'ultrafiltration time' buttons 306 are combined into an 'ultrafiltration rate+time' button 310.

In some implementations, a combined button may cause a sub-screen to be displayed that includes the individual buttons that were subject to the combination. For example, the 'ultrafiltration rate' button 304 and the 'ultrafiltration time' button 306 may be combined into an 'ultrafiltration parameters' button. When the user interacts with the 'ultrafiltration parameters' button, the touch screen display 118 may present an ultrafiltration parameters sub-screen that includes the 'ultrafiltration rate' button 304 and the 'ultrafiltration time' button 306. The user can interact with each individual button to select and adjust parameters associated with the particular button.

In some implementations, the voice command may include a reference to a stored profile that defines an arrangement of buttons to be displayed and cause the buttons to be arranged (e.g., by the user interface component 206) according to the stored profile. For example, the voice command may include a reference to a stored profile that defines a particular arrangement of buttons to be displayed. The stored profile may define one or more particular buttons to be displayed. For example, a profile may be stored that includes a modified version of the dialysis home screen on which particular buttons have been arranged. In some implementations, the screen includes one or more combined buttons. In some implementations, the stored profiles may include rearrangements and/or combinations of the following user interface elements: meter boxes, toggle buttons, action buttons, edit buttons, or the like.

The stored profile may be associated with a particular user such that certain buttons are presented and/or the buttons have a predefined arrangement when the particular user is accessing the dialysis system 100 In this way, the command to rearrange buttons may be carried out based at least in part on an identity of the user (e.g., the source of the command). For example, a particular user may have a stored profile that is associated with the particular user. The stored profile may include data representing a preconfigured set of buttons that may be in a preconfigured arrangement. The dialysis system 100 can identify the source of the voice command (as described in more detail below) and cause the buttons to be arranged according to the stored profile, e.g., by reading the data of the stored profile and using the data to determine the preconfigured arrangement. Rather than or in addition to being associated with a particular user, the stored profile may be associated with a type of user and/or a medical qualification of the user. For example, the stored profiles may include a caregiver profile (e.g., doctor or nurse), a patient profile (e.g., adult or child), and a technician profile, among others. The dialysis system 100 can identify the source of the voice command, obtain information related to the source of the voice command, and access the appropriate stored profile.

Referring to FIG. 2, the authentication component 204 is configured to determine whether a source of a voice command is an authorized user of the dialysis system 100. For example, the authentication component 204 may have access to stored authorization information that identifies the access privileges of various users (e.g., caregivers, patients, etc.) to various dialysis systems. The authentication component 204 can identify the source of the voice command and compare identification information of the source of the voice command (e.g., the name, ID number, etc. of the source) to the stored authorization information to determine whether the source of the voice command is an authorized user of the particular dialysis system 100. In some implementations, the control unit 139 does not carry out the function related to the voice command unless the authentication component 204 determines that the source of the voice command is an authorized user of the dialysis system 100.

The authentication component 204 can be configured to identify the source of the voice command in a number of ways. In some implementations, the source of the voice command verbally provides identification information that is received by the authentication component 204 through the microphone 143. The identification information may be in the form of the source's name, the source's identification number, a voice code, or the source's title/profession (e.g., doctor, nurse, technician, patient, etc.), among others.

Figure 4:
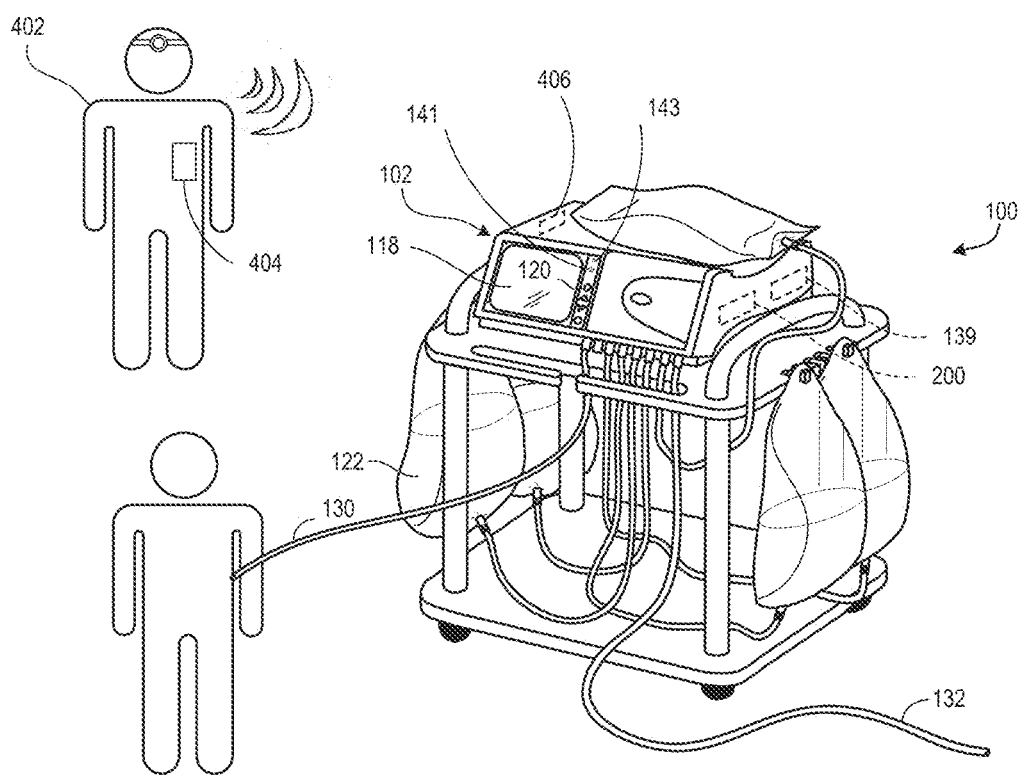
FIG. 4 shows an example of the dialysis system of FIG. 1 receiving a voice command from a user.

In some implementations, the authentication component 204 is configured to receive non-voice input (e.g., input from a non-voice interface) to identify the source of the voice command. For example, referring to FIG. 4, a doctor 402 who is the source of a voice command may carry a wireless identification device 404, such as a card that utilizes a Near Field Communication (NFC) standard. The PD machine 102 can include a wireless initiator 406, such as an NFC initiator, that is in communication with the processing component 200. The wireless initiator 406 generates an RF field that can power the wireless identification device and allow the wireless identification device 404 to provide information to the wireless initiator 406. The wireless identification device 404 is configured to provide the doctor's 402 identification information to the dialysis system 100 when the wireless identification device 404 is in proximity to the PD machine 102. For example, when the wireless identification device 404 is within transmission range of the PD machine 102, the PD machine 102 infers that the identity of the source of the voice command corresponds to the identification information provided by the wireless identification device 404. In this example, the PD machine 102 determines that the source of the voice command is the doctor 402 and that the doctor 402 is an authorized user of the PD system 102. Thus, the PD machine 102 carries out the functions related to the particular voice command. The wireless identification device 404 and the wireless initiator 406 may use other protocols such as Bluetooth™ or RFID to provide and receive the identification information.

In some implementations, the voice recognition component 202 operates in one of two states: an enabled state in which the voice recognition component 202 is configured to identify one or more voice commands in received audio information, and a standby state in which the voice recognition component 202 is configured to not identify the voice command in the audio information. While in the standby state, the voice recognition component 202 may be configured to identify a wakeup command in the audio information received by the microphone 143. The voice recognition component 202 may identify the wakeup command using an approach similar to the one described above for identifying voice commands in the audio information. For example, the voice recognition component 202 can translate the audio information into text, and the translated text can be compared to stored wakeup command information. A wakeup command may be identified based on the comparison. If a wakeup command is identified, the voice recognition component 202 enters the enabled state, in which the voice recognition component 202 can identify voice commands. In some implementations, the audio information can contain i) a wakeup command to cause the voice recognition component 202 to enter the enabled state, and ii) a subsequent voice command that can be identified by the voice recognition component 202 in the enabled state.

The stored wakeup command information may include text strings that correspond to a wakeup command. For example, a text string "hey machine number" or "wake up" followed by an identification number of the dialysis machine 102 (e.g., "hey machine number 357"; "wake up machine number 357") may cause the voice recognition component 202 of dialysis machine number 357 to enter the enabled state. In some implementations, simply reciting the identification number of a dialysis machine may cause the voice recognition component 202 of that dialysis machine to enter the enabled state.

In some implementations, the voice recognition component 202 operates in either the enabled state or the standby based on a proximity of a user to the dialysis system 100. For example, the voice recognition component 202 may operate in the enabled state while the user is within a particular distance of the dialysis system 100, and the voice recognition component 202 may operate in the standby state while the user is outside of the particular distance. The proximity of the user to the dialysis system 100 may be determined based on information received from a wireless device (e.g., an external tag that utilizes a Near Field Communication (NFC) standard). The wireless device may use a Bluetooth™ and/or an RFID protocol to provide information to the dialysis system 100. For example, the wireless device may be an RFID tag that communicates with the dialysis system 100 such that the dialysis system 100 can determine a distance between the RFID tag and the dialysis system 100. The voice recognition component 202 may operate in the enabled state while the RFID tag is within a particular distance of the dialysis system 100.

In some implementations, the voice recognition component 202 considers the particular identity of the user before considering the proximity of the user (e.g., for purposes of determining whether to operate in the enabled state or the standby state). For example, the voice recognition component 202 may determine that a user is within a particular distance of the dialysis system 100, but if the user is not an authorized user of the dialysis system 100, the voice recognition component 202 may remain in the standby state, and thus refrain from identifying voice commands. The identity of the user can be determined according to any of the examples provided above with respect to identifying the source of the voice command.

Voice Alarms/Instructions

Figure 5:
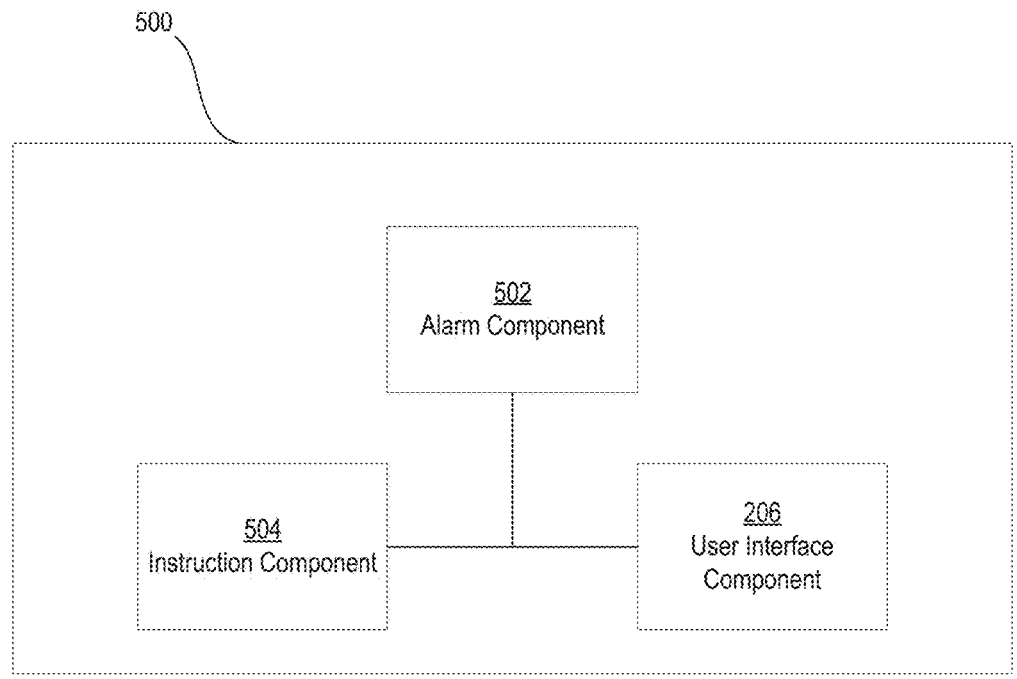
FIG. 5 shows an example of a processing component of the dialysis system of FIG. 1 that includes an alarm component, an instruction component, and a user interface component.

In some implementations, the processing component is also configured to cause voice alarms and voice instructions to be presented. FIG. 5 shows another example of a processing component 500 that includes an alarm component 502, an instruction component 504, and the user interface component (206 of FIG. 2). The processing component 500 is configured to interact with the control unit 139, the speaker 141, and the touch screen display 118 of FIG. 1.

The alarm component 502 is configured to determine whether an alarm condition related to the dialysis machine 102 exists, and cause the speaker 141 to provide spoken (e.g., verbal) information related to the alarm condition. Spoken alarm information can provide more information than traditional unspoken alarms (e.g., flashing lights, monotone/multitoned alarms). The spoken information can include the name of the patient being treated, an identification of the dialysis machine 102, and the particular alarm condition that exists. For example, if patient John Doe is being treated by dialysis machine number 357 and a blood leak is detected, the speaker 141 may emit "John Doe, machine 357, blood leak." Rather than or in addition the particular machine number, the spoken information may include other identification information related to the particular dialysis machine, such as a location of the machine. In some implementations, the touch screen display 118 can display information related to the alarm condition when the alarm condition arises. A user can interact with the touch screen display 118 (e.g., by selecting an alarm status box) to obtain more detailed alarm information, such as particular values for various measurements that led to the alarm condition.

Figure 6:
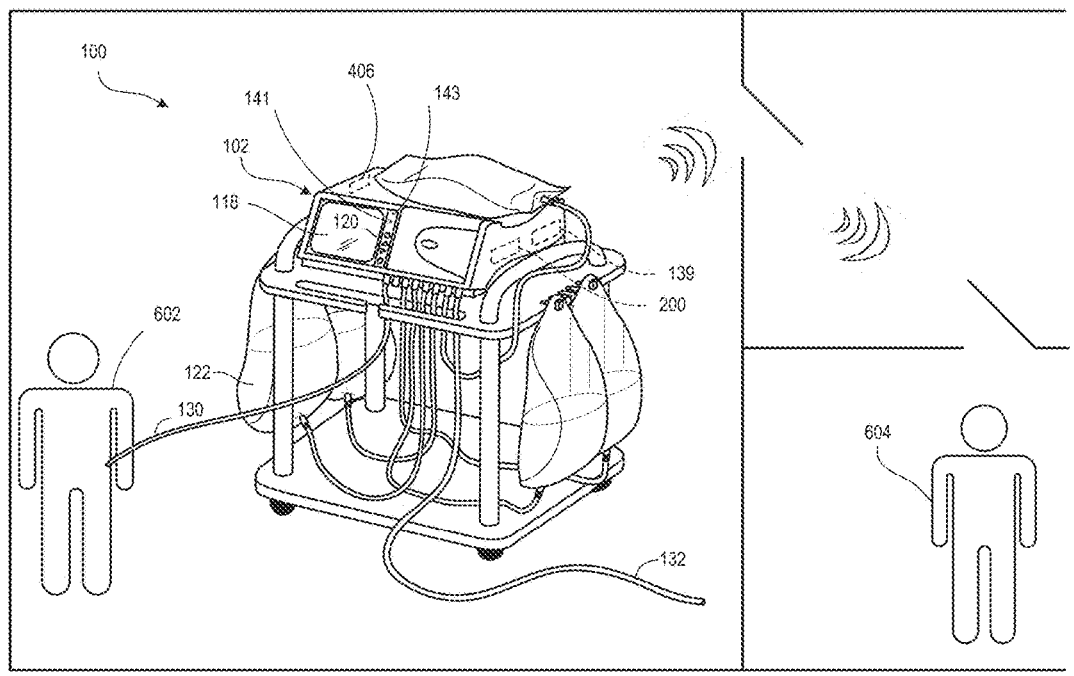
FIG. 6 shows an example of the dialysis system of FIG. 1 providing spoken alarm information.

The spoken alarm information may be useful in home dialysis contexts. For example, spoken information that includes information related to the particular alarm condition can assist a caregiver or a guardian in quickly identifying dangerous or life-threatening situations. FIG. 6 shows an example of a child patient 602 receiving a treatment from the PD machine 102 with the supervision of the child's parent 604. If the parent 604 temporarily leaves the child alone by going to an adjacent room, he or she may be unable to closely monitor the dialysis treatment for a period of time. If a serious alarm condition arises (e.g., a blood leak alarm condition, an air detection alarm condition, a high/low temperature alarm condition, an arterial pressure low/high alarm condition, a pulse low/high alarm condition, or a systolic pressure low/high alarm condition, among others), the parent 604 will hear the spoken alarm, which includes the particular condition being experienced, and know that immediate assistance is needed. On the other hand, if a relatively non-serious alarm condition arises (e.g., a "missing bicarbonate bag" alarm condition or an "unexpected bicarbonate bag" alarm condition, among others), the parent 604 will know that the condition is not critical. Such detailed alarm information can also be especially helpful for patients and/or caregivers with a visual impairment who would otherwise be unable to ascertain the particular alarm condition.

The spoken alarm information may also be useful in environments that include multiple dialysis machines, such as dialysis clinics, to assist the caregiver in differentiating various alarms that may be occurring concurrently. For example, if three alarm conditions exist concurrently for three different dialysis machines, the caregiver can quickly identify the types of each alarm condition, determine which alarm condition is the most critical, and provide assistance to the patient according to need.

The instruction component 504 is configured to cause spoken instructions to be provided to a user of the dialysis system 100. The instruction component 504 can determine whether a particular action has been completed. If the instruction component 504 determines that the particular action has not yet been completed, the instruction component 504 can cause the speaker 141 to provide spoken instructions that can assist a user of the dialysis system 100 in completing the particular action. Such actions can include set up actions, treatment actions, and calibration actions, among others. The spoken instructions may be provided automatically (e.g., upon determining that the action has not yet been completed and/or after a predetermined amount of time relative to machine initiation) or in response to the user interacting with the dialysis system 100 (e.g., upon the user interacting with the touch screen display 118, as described in more detail below).

For example, the instruction component 504 may determine that a portion of machine set up has not yet been completed. The instruction component 504 can cause the speaker 141 to provide spoken instructions that assist the patient and/or a caregiver in setting up the dialysis system 100. In this way, the spoken instructions may also act as an alert indicating that one or more actions need to be completed. The spoken instructions can include step-by-step directions for completing the actions. For example, the instruction component 504 may provide spoken step-by-step directions for preparing the patient for a dialysis treatment, with each spoken step corresponding to an action. The instructions can include the following spoken steps: i) "ensure heater tray is free from obstructions"; ii) "insert cassette into cassette compartment"; iii) "connect dialysate bags to cassette via dialysate bag lines"; iv) "place heater bag on heater tray"; v) "connect heater bag to cassette via heater bag line"; vi) "connect drain line to cassette and drain"; vii) "connect patient line to cassette and to patient via catheter"; and viii) "clamp unused lines."

The spoken instructions can be automatically provided in sequence such that there are delays between the spoken steps. In some implementations, the delays are predefined, and each delay has a length that is based on the approximate amount of time that it typically takes for the user to perform the action that corresponds to the previous spoken step. In some implementations, one or more portions of the spoken instructions (e.g., one or more of the spoken steps) are provided in response to the user interacting with the dialysis system 100.

In some implementations, the user interface (e.g., the touch screen display 118) is configured to provide visual information related to the action. FIGS. 7A-D show examples of the touch screen display 118 providing visual information that includes images that show a representation of the action being partially or fully completed. In some implementations, the visual information includes videos in addition to or instead of images.

Figure 7A:
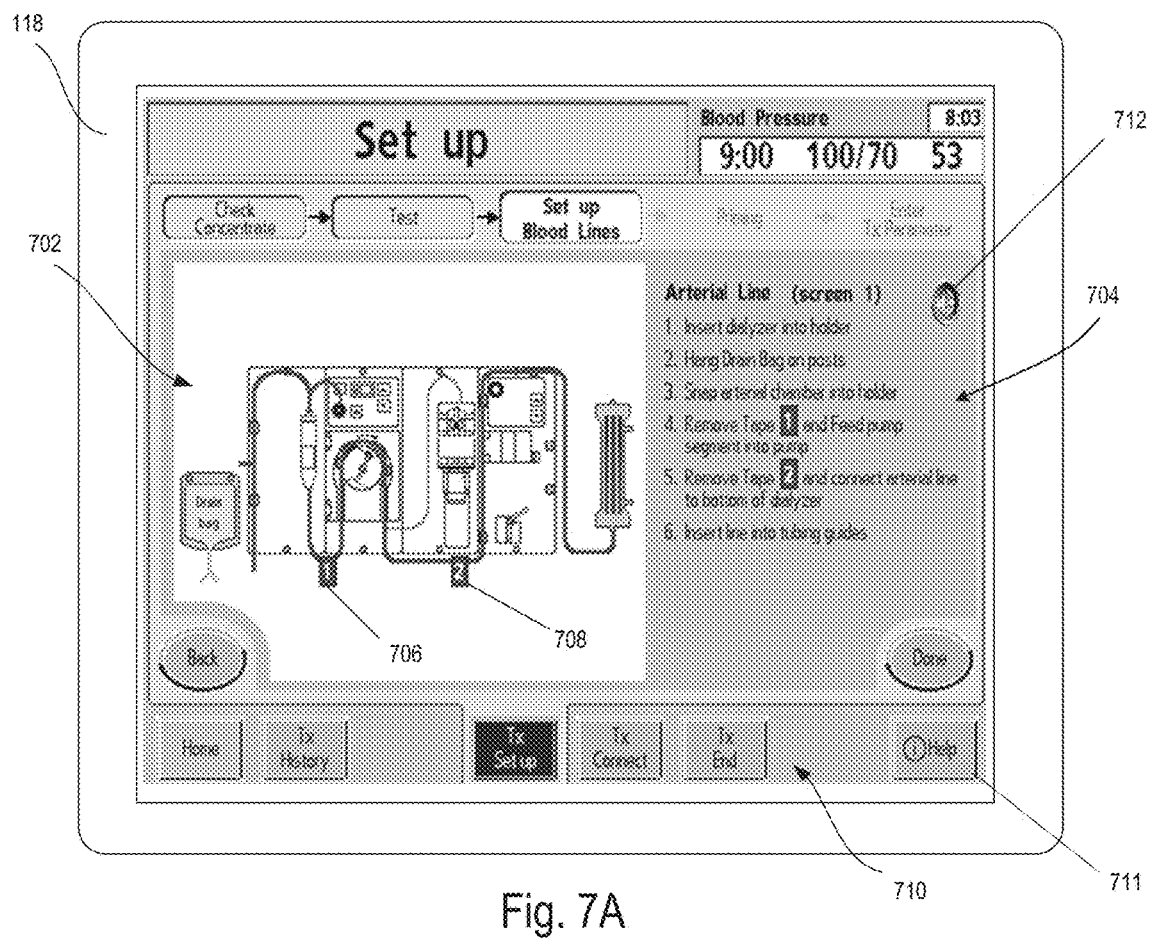
FIGS. 7A-D show examples of visual information provided by a user interface of the dialysis system of FIG. 1.

FIG. 7A shows an example of the touch screen display 118 providing visual information related to setting up the arterial line, as described above. The visual information includes an image 702 that shows a representation of components of the dialysis system 100 relevant to setting up the arterial line, and written instructions 704 for performing the action. In some implementation, the image 702 is modified as each step of the written instructions 704 is provided by the speaker 141. For example, when the "remove tape and feed pump segment into pump" instruction is provided, a first indicator 706 may be highlighted to assist the user in finding the tape that should be removed. Similarly, when the "remove tape and connect arterial line to bottom of dialyzer" instruction is provided, a second indicator 708 may be highlighted. The touch screen display 118 also presents category buttons 710 that the user can interact with to cause visual information related to different actions to be displayed.

Figure 7B:
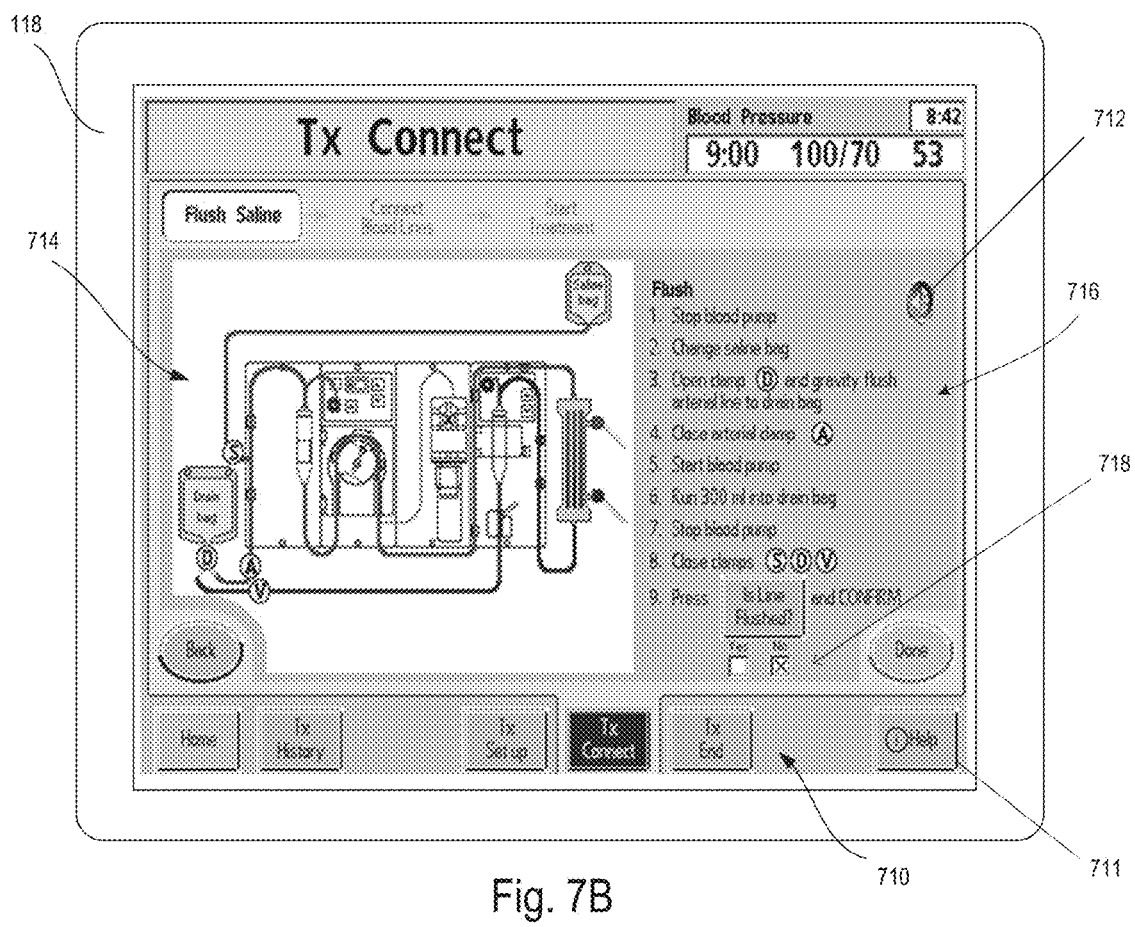

FIG. 7B shows an example of the touch screen display 118 providing visual information related to flushing saline. The visual information includes an image 714 that shows a representation of components of the dialysis system 100 relevant to flushing saline, and written instructions 716 for performing the action. The image 714 includes various indicators (denoted by the letters "A", "D", "S", and "V") that correspond to portions of the written instructions 716 for assisting the user in performing the flush saline action. As mentioned above, the image 714 may be modified to add and/or highlight the indicators as each step of the written instructions 714 is provided by the speaker 141. For example, when the "open clamp and gravity flush arterial line to drain bag" instruction is provided, the "D" indicator may be highlighted to assist the user in finding the clamp. The written instructions 716 can also include additional buttons that the user can interact with while performing the actions. In this example, the written instructions 716 include checkboxes 718 for confirming that the line has been flushed. In some implementations, the user confirms that an action has been completed (e.g., by checking the "yes" checkbox) to cause the next instruction to be provided.

Figure 7C:
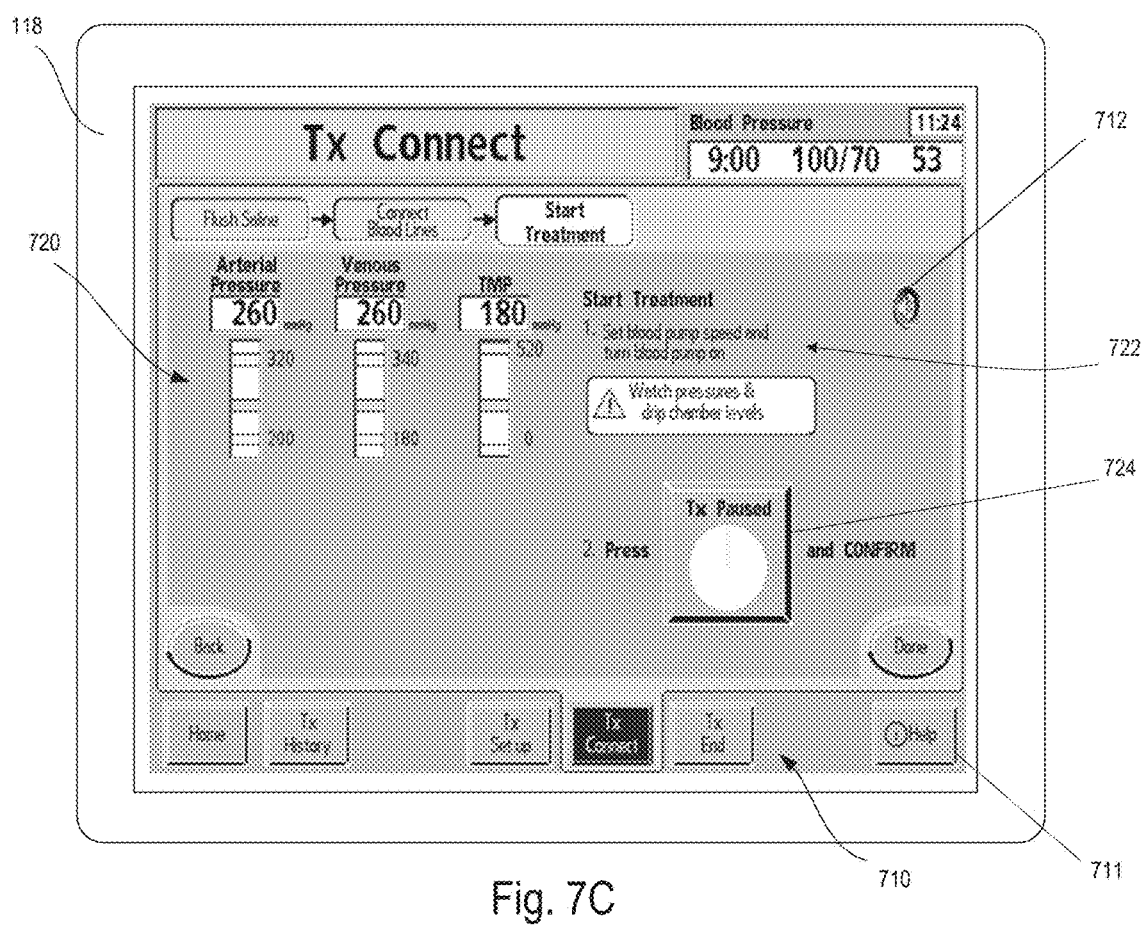

FIG. 7C shows an example of the touch screen display 118 providing visual information related to starting a treatment. The visual information includes an image 720 that shows a representation of parameters (e.g., arterial pressure, venous pressure, transmembrane pressure (TMP)) relevant to starting a treatment, and written instructions 722 for performing the action. The written instructions 722 also include a 'Tx' button 724 that the user can interact with to start the treatment. In this example, the 'Tx' button 724 is in the paused state. After the "set blood pump speed and turn blood pump on" instruction is provided and the user performs the action, the user can interact with the 'Tx' button 724 to cause the dialysis system 100 to start the treatment.

Figure 7D:
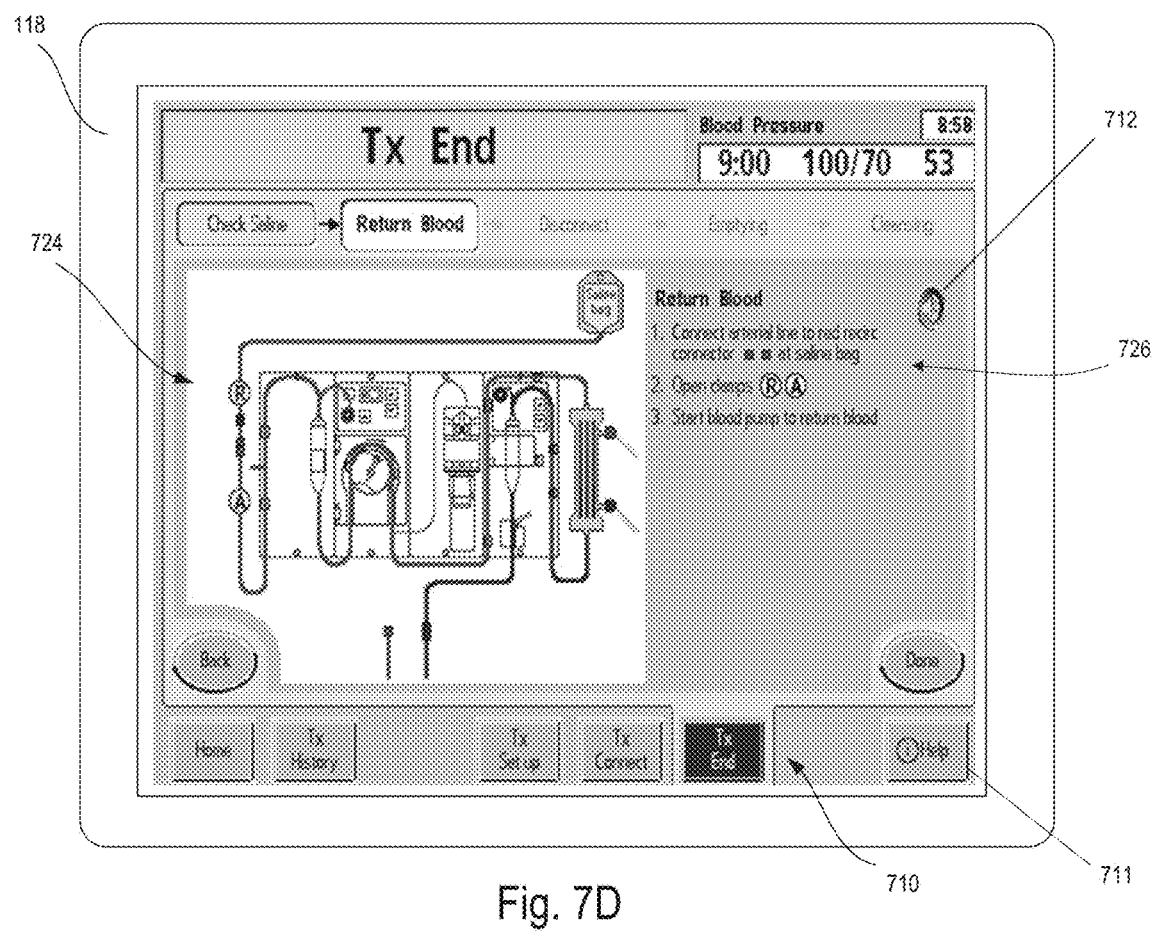

FIG. 7D shows an example of the touch screen display 118 providing visual information related to ending a treatment. The visual information includes an image 724 that shows a representation of components of the dialysis system 100 relevant to ending the treatment, and written instructions 726 for performing the action. As in some of the previous examples, the image 724 includes various indicators (denoted by the letters "R" and "A") that correspond to portions of the written instructions 726 for assisting the user in ending the treatment. The image 714 may be modified to add and/or highlight the indicators as each step of the written instructions 714 is provided by the speaker 141.

As mentioned above, in some implementations, one or more portions of the spoken instructions (e.g., one or more of the spoken steps that correspond to actions) are provided in response to the user interacting with the dialysis system 100. Referring to FIGS. 7A-7D, the touch screen display 118 can provide a 'play' button 712. The user may interact with the 'play' button 712 to cause the spoken instructions to be provided by the speaker 141. In some implementations, all steps of the spoken instructions are provided in series upon the user interacting with the 'play' button 712, and the user can perform the associated actions as the spoken instructions are provided. In some implementations, a first step of the spoken instructions is provided upon the user interacting with the 'play' button 712, and each subsequent step is provided upon the user again interacting with the 'play' button 712, thereby ensuring that the user has sufficient time to perform each actions. In some implementations, the user can interact with the 'play' button 712 to pause playback of the spoken instruction. In some implementations, the user can interact with the 'play' button 712 after the spoken instructions have been provided to cause the spoken instructions to be repeated. In some implementations, the dialysis system 100 can detect when a particular action has been performed, and in response, cause a subsequent spoken instruction to be provided.

Still referring to FIGS. 7A-7D, the touch screen display 118 can provide a 'help' button 711 that the user can interact with to access a help screen. In some implementations, the 'help' button 711 also performs the functionality of the 'play' button 712 described above. For example, upon interacting with the 'help' button 711, the touch screen display 118 may present a dialog for allowing the user to i) access the help screen, or ii) initiate the spoken instructions. In some implementations, the functionality of the 'help' button 711 and the 'play' button 712 can be combined into a single 'help/play' button. In some implementations, interacting with the 'help' button 711 may cause the touch screen display 118 to play a video that shows a particular action being performed to assist the user in performing the particular action.

The verbosity (e.g., the types of details, the level of detail, etc.) of the spoken alarm information and/or the spoken instruction can be adjustable. For example, in the context of spoken alarm information, the verbosity may be based on a qualification (e.g., a medical qualification) of the target user because certain users may benefit from more or less details related to the alarm condition. If the target user is not a medical professional (e.g., the target user is a patient), a minimal verbosity setting may be employed by the dialysis system 100 (e.g., "arterial pressure alarm, check patient and arterial port"). On the other hand, if the target user is a caregiver (e.g., the target user is a doctor or a nurse), a more extensive verbosity setting may be employed to convey additional information (e.g., "arterial pressure alarm, arterial pressure of 50 mmHg detected, check patient and arterial port"). In the context of spoken instructions, the verbosity may also be based on an identity and/or a medical qualification of the target user. If the target user is not a medical professional, an extensive verbosity setting may be employed (e.g., "insert dialyzer into holder"; ii) "hang drain bag on posts"; iii) "snap arterial chamber into holder"; iv) "remove tape 1 and feed pump segment into pump"; v)"remove tape 2 and connect arterial line to bottom of dialyzer"; and iv) "insert line into tubing guides"). In some implementations, such relatively extensive verbosity setting cause indicators (e.g., 706, 708 of FIG. 7A) to be included in the image 702 and the written instructions 704 that correspond to the spoken instructions. On the other hand, if the target user is a caregiver, a less extensive verbosity setting may be employed (e.g., "set up blood line"). In some implementations, an alternative verbosity setting may be employed if the target user is a machine technician. For example, the spoken instructions may include a high level of detail that is relevant for troubleshooting and/or performing maintenance on the dialysis system 100.

The verbosity may also be based on an identity of a particular user. For example, a particular verbosity setting may correspond to each of a number of particular users. Information related to such correspondences may be stored on the dialysis system 100 and/or stored in a location accessible by the dialysis system 100 (e.g., on a server, in a database, etc.).

The qualification and/or identity of the user may be determined in a number of ways. In some implementations, the user verbally provides identification information to the dialysis system 100 (e.g., the user's name, identification number, and/or title/profession) using the techniques described above. In some implementations, the user provides such identification through the touch screen display 118 and/or the control panel 120. In some implementations, the qualification and/or identity of the user is determines using non-voice input (e.g., input provided by a wireless communication device). For example, the qualification and/ or the identity of the user may be determined based on information provided by a wireless identification device associated with the user, such as the wireless identification device 404 of FIG. 4.

In some implementation, the verbosity of the spoken alarm information and/or the spoken instruction can be manually adjusted by a user. For example, the user may access a settings screen that allows configuration of the verbosity by interacting with a user interface element presented by the touch screen display 118. Briefly referring back to FIGS. 7A-7D, the user may interact with the 'help' button 711 to cause a verbosity adjustment window to be presented.

While certain implementations have been described, other implementations are possible.

Figure 8:
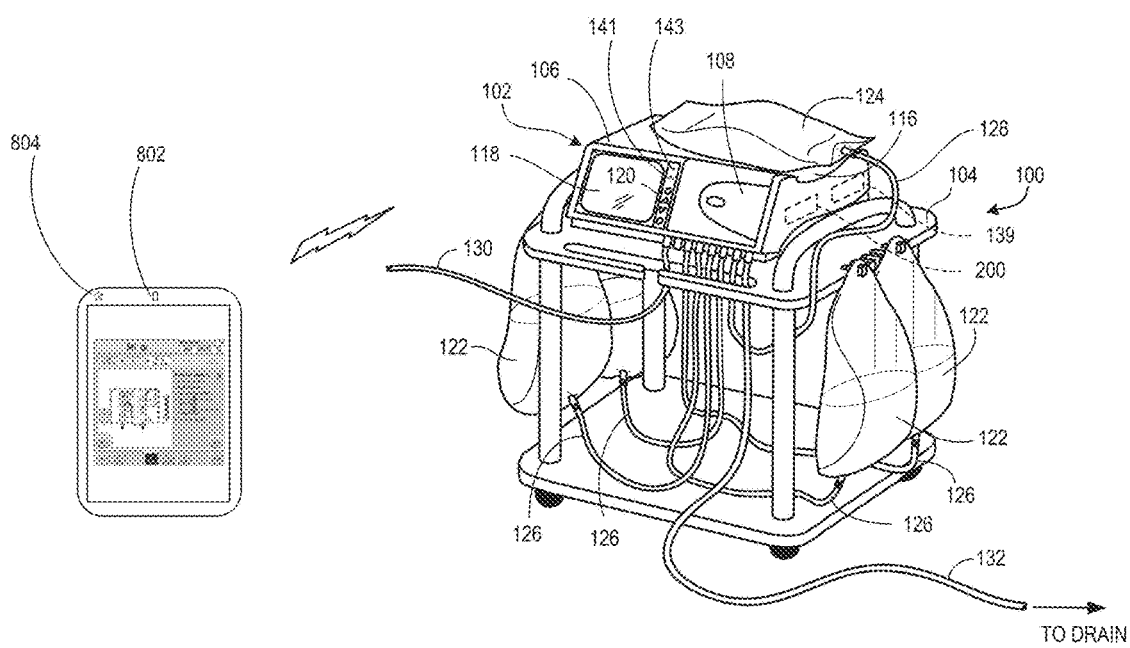
FIG. 8 shows an example of the dialysis system of FIG. 1 in communication with an external device that includes a microphone and a speaker.

While the dialysis system has been described as including the microphone and the speaker, in some implementations, one or both of the microphone and the speaker is part of a separate, external device. FIG. 8 shows an example of a tablet computer 800 that is configured to communicate (e.g., wirelessly communicate) with the dialysis system 100. The tablet computer 800 includes a microphone 802 and a speaker 804. The microphone 802 and the speaker 804 may be included in addition to or instead of the microphone 143 and the speaker 141 of the dialysis system 100. The microphone 802 is configured to receive audio information (e.g., spoken information) from a user and provide the audio information to the dialysis system 100. The voice recognition component (202 of FIG. 2) receives the audio information and can identify one or more voice commands in the audio information using the techniques described above.

Voice alarms and/or voice instructions can be provided by the speaker 804. For example, when the alarm component (502 of FIG. 5) determines that an alarm condition exists, the dialysis system 100 can provide information to the tablet computer 800 that causes the speaker 804 to provide spoken information related to the alarm condition. Similarly, when the instruction component (504 of FIG. 5) determines that voice instructions are to be provided (e.g., based on a determination that a particular action has not yet been completed), the dialysis system 100 can provide information to the tablet computer 800 that causes the speaker 804 to provide spoken instructions for assisting a user in completing the action.

While the external device has been described as being a tablet computer, in some implementations, the external device is another type of external computing device such as a laptop, a smartphone, or a personal digital assistant (PDA), among others.

While the processing component has been described as including the voice recognition component, in some implementations, the voice recognition component is part of the external device. For example, the external device may include a microphone that receives audio information, the voice recognition component can translate the audio information into text, and the external device can provide the translated text to the dialysis system. In some implementations, rather than the translated text being provided directly to the dialysis system, the translated text is compared to stored information (e.g., stored text) that corresponds to one or more voice commands, and the external device instead provides information related to the invoked voice command to the dialysis system. The dialysis system can then carry out a function related to the voice command.

In some implementations, a display of the external device can replicate what is presented by the touch screen display of the dialysis system. For example, user interface elements (e.g., buttons), images, videos, and/or written instructions that are presented by the touch screen display may also be displayed on the external device. In some implementations, the external device's display is a touch screen display. In some implementations, a user can interact with the external device in the same way that the user can interact with the dialysis system's touch screen display in order to control the dialysis system. The ability to control the dialysis system using the external device may require authentication (e.g., by the authentication component) according to the procedures described above.

While the control unit and the processing component have been described as being separate components, in some implementations, the control unit is part of the processing component. In some implementations, the processing component is part of the control unit. In some implementations, the dialysis machine includes multiple control units and/or processing components.

While various different components of the dialysis machine (e.g., the voice recognition component, the authentication component, the user interface component, the alarm component, the instruction component, etc.) have been described, in some implementations, the functionality of the various components can be performed by one or more control units and/or processors. For example, in some implementations, the dialysis machine includes one processor (e.g., the control unit 139 of FIG. 1) that is configured to perform the functionality of the voice recognition component, the authentication component, the user interface component, the alarm component, and the instruction component, among others.

While the processing component has been described as having various embodiments that include various components (e.g., the voice recognition component, the authentication component, the user interface component, the alarm component, the instruction component, etc.), in some implementations, the processing component can include additional components, fewer components, or different combinations of components. For example, the processing component may include a different combination of components than those shown in the figures. In some implementations, a single processing component includes all of the various components described herein.

In some implementations, multiple voice commands can be received and queued up by the dialysis system. For example, the microphone can receive audio information that includes multiple voice commands, and the control unit can execute the voice commands in a particular order. For example, the voice commands may be executed in the order in which they were received. In some implementations, the voice commands are executed according to other criteria (e.g., based on predefined rules or configuration parameters of the dialysis system). For example, a first voice command may be received that corresponds to a relatively trivial function, and a second voice command may subsequently be received that corresponds to a relatively urgent function. The second voice command may be executed before the first voice command based on predefined priority information. The multiple voice commands may be separated by the word "then" to signify that multiple voice commands are being provided.

In some implementations, the user interface may be configured to present a particular screen upon the dialysis system receiving a voice command. For example, if a user provides a "set dialysate flow rate" voice command while the user interface is presenting a home screen, the user interface may automatically switch to presenting a dialysis set up screen (e.g., a screen for setting a dialysate flow rate).

While the voice commands have been largely described as causing the dialysis system to perform dialysis treatment configuration functions and user interface configuration functions, in some implementations, one or more of the voice commands are related to dialysis machine maintenance functions and/or cleaning functions. For example, the voice commands may include a command for causing the dialysis machine to update its software and/or firmware, causing the dialysis machine to reboot, causing the dialysis machine to shut down, and/or causing the dialysis machine to initiate a rinse cycle, among others.

While examples of voice commands that cause the arrangement of user interface element (e.g., buttons) to be rearranged have been described, in some implementations, the dialysis system may also allow for manual reconfiguration of the buttons. For example, a user may manually configure the buttons in a particular arrangement and instruct the dialysis system to save the arrangement. When the user subsequently accesses the dialysis system, the saved configuration may be restored.

While the dialysis system has been largely described as being a peritoneal (PD) dialysis system, other medical treatment systems can employ the techniques described herein. Examples of other medical treatment systems include hemodialysis systems, hemofiltration systems, hemodiafiltration systems, apheresis systems, and cardiopulmonary bypass systems.

Figure 9:
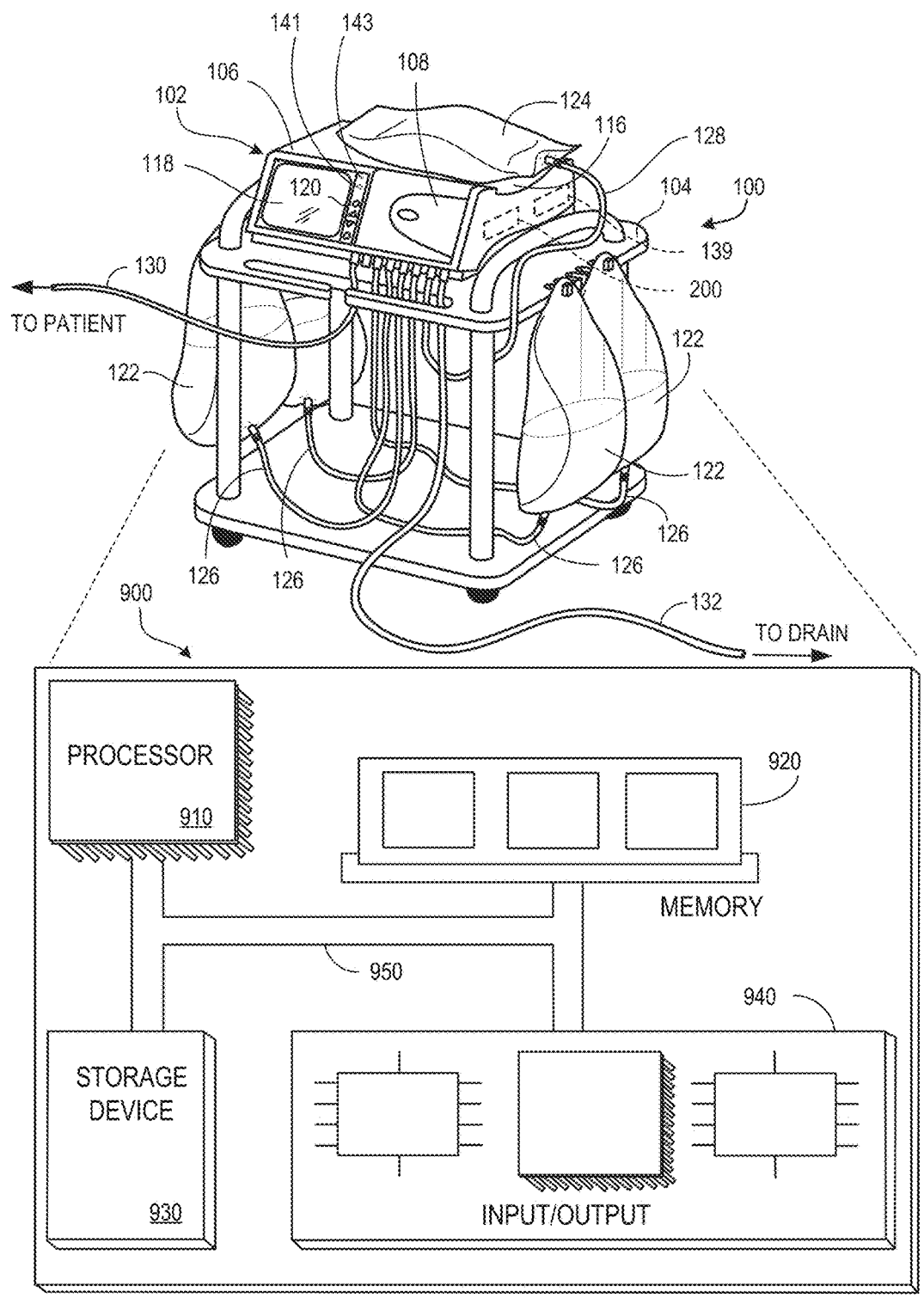
FIG. 9 shows an example of a computer system.

FIG. 9 is a block diagram of an example computer system 900. For example, referring to FIGS. 1, 2, and 5, the control unit 139 and/or the processing component(s) 200, 500 could be examples of the system 900 described here. The system 900 includes a processor 910, a memory 920, a storage device 930, and an input/output device 940. Each of the components 910, 920, 930, and 940 can be interconnected, for example, using a system bus 950. The processor 910 is capable of processing instructions for execution within the system 900. The processor 910 can be a single-threaded processor, a multi-threaded processor, or a quantum computer. The processor 910 is capable of processing instructions stored in the memory 920 or on the storage device 930. The processor 910 may execute operations such as causing the dialysis system to carry out functions related to voice commands, voice alarms, and voice instructions.

The memory 920 stores information within the system 900. In some implementations, the memory 920 is a computer-readable medium. The memory 920 can, for example, be a volatile memory unit or a non-volatile memory unit. In some implementations, the memory 920 stores information (e.g., text) that corresponds to one or more voice commands and/or wakeup commands, profiles that define arrangements of buttons to be displayed by a user interface (e.g., the touch screen display 118), authentication information that identifies access privileges of various users of the dialysis system 100, and/or information related to verbosity settings.

The storage device 930 is capable of providing mass storage for the system 900. In some implementations, the storage device 930 is a non-transitory computer-readable medium. The storage device 930 can include, for example, a hard disk device, an optical disk device, a solid-date drive, a flash drive, magnetic tape, or some other large capacity storage device. The storage device 930 may alternatively be a cloud storage device, e.g., a logical storage device including multiple physical storage devices distributed on a network and accessed using a network.

The input/output device 940 provides input/output operations for the system 900. In some implementations, the input/output device 940 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (such as the touch screen display 118). In some implementations, mobile computing devices, mobile communication devices, and other devices are used.

In some implementations, the system 900 is a microcontroller. A microcontroller is a device that contains multiple elements of a computer system in a single electronics package. For example, the single electronics package could contain the processor 910, the memory 920, the storage device 930, and input/output devices 940.

Although an example processing system has been described in FIG. 9, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed is:

1. A dialysis system comprising:
   a dialysis machine;
   a speaker; and
   an alarm component configured to:
      determine that an alarm condition related to the dialysis machine exists; and
      cause the speaker to provide spoken information related to the alarm condition,
   wherein the alarm component is configured to determine the spoken information based on a verbosity setting of the dialysis system.

2. The dialysis system of claim 1, wherein the spoken information comprises an identification of the dialysis machine.

3. The dialysis system of claim 2, wherein the identification of the dialysis machine comprises a machine number.

4. The dialysis system of claim 1, wherein the spoken information comprises an identification of a location of the dialysis machine.

5. The dialysis system of claim 1, wherein the spoken information comprises a name of a user of the dialysis system.

6. The dialysis system of claim 1, wherein the verbosity setting is determined based on an identity of a user of the dialysis system.

7. The dialysis system of claim 6, wherein information related to the verbosity setting that corresponds to the user is stored on a server.

8. The dialysis system of claim 1, wherein the verbosity setting is determined based on a medical qualification of a user of the dialysis system.

9. A dialysis system comprising:
   a dialysis machine;
   a speaker; and
   an instruction component configured to:
      determine that an action has not yet been completed; and
      cause the speaker to provide spoken instructions that assist a user of the dialysis system in completing the action,
   wherein the instruction component is configured to determine the spoken instructions based on a verbosity setting of the dialysis system.

10. The dialysis system of claim 9, wherein the verbosity setting is determined based on an identity of the user.

11. The dialysis system of claim 10, wherein information related to the verbosity setting that corresponds to the user is stored on a server.

12. The dialysis system of claim 9, wherein the verbosity setting is determined based on a medical qualification of the user.

13. The dialysis system of claim 9, wherein the instruction component is configured to cause the speaker to provide subsequent spoken instructions that assist the user of the dialysis system in completing a second action.

14. The dialysis system of claim 9, wherein the action comprises one or more of a set up action, a treatment action, and a calibration action.

15. A dialysis system comprising:
   a dialysis machine;
   a speaker; and
   an instruction component configured to:
      determine that an action has not yet been completed; and
      cause the speaker to provide spoken instructions that assist a user of the dialysis system in completing the action,
   wherein the subsequent spoken instructions are provided one or both of: i) a predetermined amount of time after the spoken instructions are provided, or ii) in response to the user interacting with the dialysis system after the action is completed.

16. A dialysis system comprising:
   a dialysis machine;
   a speaker;
   an instruction component configured to:
      determine that an action has not yet been completed; and
      cause the speaker to provide spoken instructions that assist a user of the dialysis system in completing the action; and
   a display that is configured to provide visual information related to the action,
   wherein the visual information is one or both of an image or a video that show the action being at least partially completed.

* * * * *